(12) United States Patent
Vardanega

(10) Patent No.: US 7,905,911 B2
(45) Date of Patent: Mar. 15, 2011

(54) METHOD AND APPARATUS FOR CONNECTING A HOSE TO A WARMING BLANKET

(75) Inventor: Michael Vardanega, Livermore, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 879 days.

(21) Appl. No.: 11/528,294

(22) Filed: Sep. 27, 2006

(65) Prior Publication Data

US 2008/0077209 A1 Mar. 27, 2008

(51) Int. Cl.
*A61F 7/00* (2006.01)
(52) U.S. Cl. ...................................... 607/107; 607/104
(58) Field of Classification Search ........... 607/104–112
See application file for complete search history.

(56) References Cited

U.S. PATENT DOCUMENTS

| | | | |
|---|---|---|---|
| 2,941,907 A | 6/1960 | Tousignant et al. | |
| 3,236,370 A | 2/1966 | Pereny et al. | |
| 3,410,266 A | 11/1968 | Krzewinski et al. | |
| 3,667,458 A | 6/1972 | Krebs | |
| 3,741,206 A | 6/1973 | Binard et al. | |
| 3,750,664 A | 8/1973 | Collins | |
| 3,835,851 A | 9/1974 | Villari | |
| 3,916,887 A | 11/1975 | Kelly | |
| 4,024,862 A | 5/1977 | Collins | |
| 4,089,331 A | 5/1978 | Hartigan et al. | |
| 4,334,529 A | 6/1982 | Wirth | |
| 4,807,644 A | 2/1989 | Sandhaus | |
| 4,957,120 A | 9/1990 | Grier-Idris | |
| 5,265,599 A | 11/1993 | Stephenson et al. | |
| 5,318,568 A * | 6/1994 | Kaufmann et al. | 607/107 |
| 5,443,488 A | 8/1995 | Namenye et al. | |
| 5,545,194 A | 8/1996 | Augustine | |
| 5,728,145 A | 3/1998 | Phlipot et al. | |
| 5,735,890 A | 4/1998 | Kappel et al. | |
| 5,817,147 A | 10/1998 | Wolf | |
| 5,890,243 A | 4/1999 | Dickerhoff | |
| 6,112,348 A | 9/2000 | Dickerhoff | |
| 6,167,885 B1 | 1/2001 | Hanssen | |
| 6,168,612 B1 | 1/2001 | Augustine et al. | |
| 6,176,870 B1 | 1/2001 | Augustine | |
| 6,203,567 B1 | 3/2001 | Augustine | |
| 6,994,720 B2 | 2/2006 | Gammons | |
| 7,096,870 B2 | 8/2006 | Lamprich et al. | |
| 7,108,713 B1 | 9/2006 | Augustine | |
| 7,172,616 B2 | 2/2007 | Scheussler et al. | |
| 7,338,515 B2 * | 3/2008 | Van Duren et al. | 607/96 |
| 7,409,953 B2 | 8/2008 | Griesbach, III | |
| 7,550,000 B2 * | 6/2009 | Frey | 607/104 |
| 2003/0135251 A1 | 7/2003 | Scheussler et al. | |
| 2005/0143796 A1 * | 6/2005 | Augustine et al. | 607/104 |
| 2006/0052851 A1 | 3/2006 | Anderson et al. | |
| 2007/0093884 A1 | 4/2007 | Anderson et al. | |
| 2008/0077207 A1 | 3/2008 | Vardanega | |
| 2008/0077208 A1 | 3/2008 | Vardanega | |
| 2008/0077209 A1 | 3/2008 | Vardanega | |

\* cited by examiner

*Primary Examiner* — Roy D Gibson
(74) *Attorney, Agent, or Firm* — Fletcher Yoder

(57) ABSTRACT

A nozzle is provided for connecting an air hose to an air inlet. In one embodiment, the nozzle includes a tapered region and a plurality of vents. In another embodiment, the nozzle includes a projection configured to facilitate insertion of the nozzle into an air inlet. Warming assemblies comprising heated air blowers and warming blankets connected by the air hose and varying nozzle embodiments are also provided.

15 Claims, 3 Drawing Sheets

METHOD AND APPARATUS FOR CONNECTING A HOSE TO A WARMING BLANKET

BACKGROUND OF THE INVENTION

1. Field of the Invention

The present disclosure is generally related to materials and procedures for maintaining patient temperature.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

A variety of medical environments are commonly maintained at temperatures well below body temperature to slow microbial growth, to counter the heat generated by medical lighting or equipment, or for various other reasons. For example, operating room temperatures of 65° F. (20° C.) and below are not uncommon. At such temperatures, it may be difficult to maintain the body temperature of the patient over time, such as over the course of a diagnostic, therapeutic, or surgical procedure.

To maintain patient temperature, a convective air warming blanket may be employed in the medical environment. Such a convective air warming blanket typically consists of two die cut sheets of material that are attached (such as by radio-frequency (RF) or ultra-sonic techniques) along their edges and at numerous internal weld locations. The internal welds limit the loft, i.e., height or thickness, of the warming blanket when inflated.

After the sheets forming the warming blanket are attached, the warming blanket may be die cut into the warming blanket's final shape. This die cut process, in which the sheets are cut simultaneously using a single die, results in their being little or no structural differentiation between the two sheets, making it difficult to separate the two sheets, particularly in contexts where gloves are worn or where personnel are occupied with other tasks. As a result, techniques for inflating the warming blanket that involve inserting a warm air blowing mechanism between the sheets may be difficult to perform, in turn making the inflation of the warming blanket a difficult process.

For example, in a common implementation, health care personnel insert the nozzle end of an air hose into an opening in the warming blanket where the sheets forming the warming blanket are not sealed together. Due to the difficulty in separating these sheets and the shape of the nozzle, it may be difficult for a single person to insert the nozzle into the warming blanket.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a warming assembly. The warming assembly includes a heated air blower configured to blow heated air and a warming blanket comprising an air inlet. The warming assembly also includes a hose configured to connect the heated air blower and the warming blanket. The hose includes a tapered nozzle on an end of the hose that is inserted into the air inlet. The tapered nozzle includes a plurality of vents.

There is also provided a warming assembly. The warming assembly includes a heated air blower configured to blow heated air and a warming blanket comprising an air inlet. The warming assembly also includes a hose configured to connect the heated air blower and the warming blanket. The hose includes a nozzle on an end of the hose that is inserted into the air inlet. The nozzle also includes a projection configured to facilitate insertion of the nozzle into the air inlet.

There is also provided a nozzle configured for use with an air hose. The nozzle includes a tapered region and a plurality of vents. The nozzle is configured to be inserted into an air inlet of a warming blanket.

There is further provided a nozzle configured for use with an air hose. The nozzle includes a projection configured to facilitate insertion of the nozzle into an air inlet of a warming blanket.

There is also provided a method for inserting a nozzle into an air inlet. The method includes the act of separating two sheets forming an air inlet of a warming blanket with a projecting portion of a nozzle of an air hose. The method also includes the act of inserting the nozzle between the separated sheets of the air inlet.

BRIEF DESCRIPTION OF THE DRAWINGS

Some embodiments of the disclosure may be understood by referring, in part, to the following description and the accompanying drawings, in which like reference numbers refer to the same or like parts and wherein.

DETAILED DESCRIPTION OF SPECIFIC EMBODIMENTS

In some embodiments of the present technique, a nozzle of an air hose is employed that allows easy connection to a corresponding air inlet of a warming blanket. For example, in one embodiment, the nozzle is shaped to facilitate insertion into the corresponding inlet without significantly reducing air throughput. In one embodiment, the nozzle is shaped such that a portion of the nozzle acts as a scoop or separating mechanism to separate the individual sheets forming the inlet in which the nozzle is to be inserted. In some embodiments, the nozzle also includes vents (such as along the sides of the nozzle) that allow air to exit the nozzle at locations other than the primary nozzle output opening.

Figure 1:
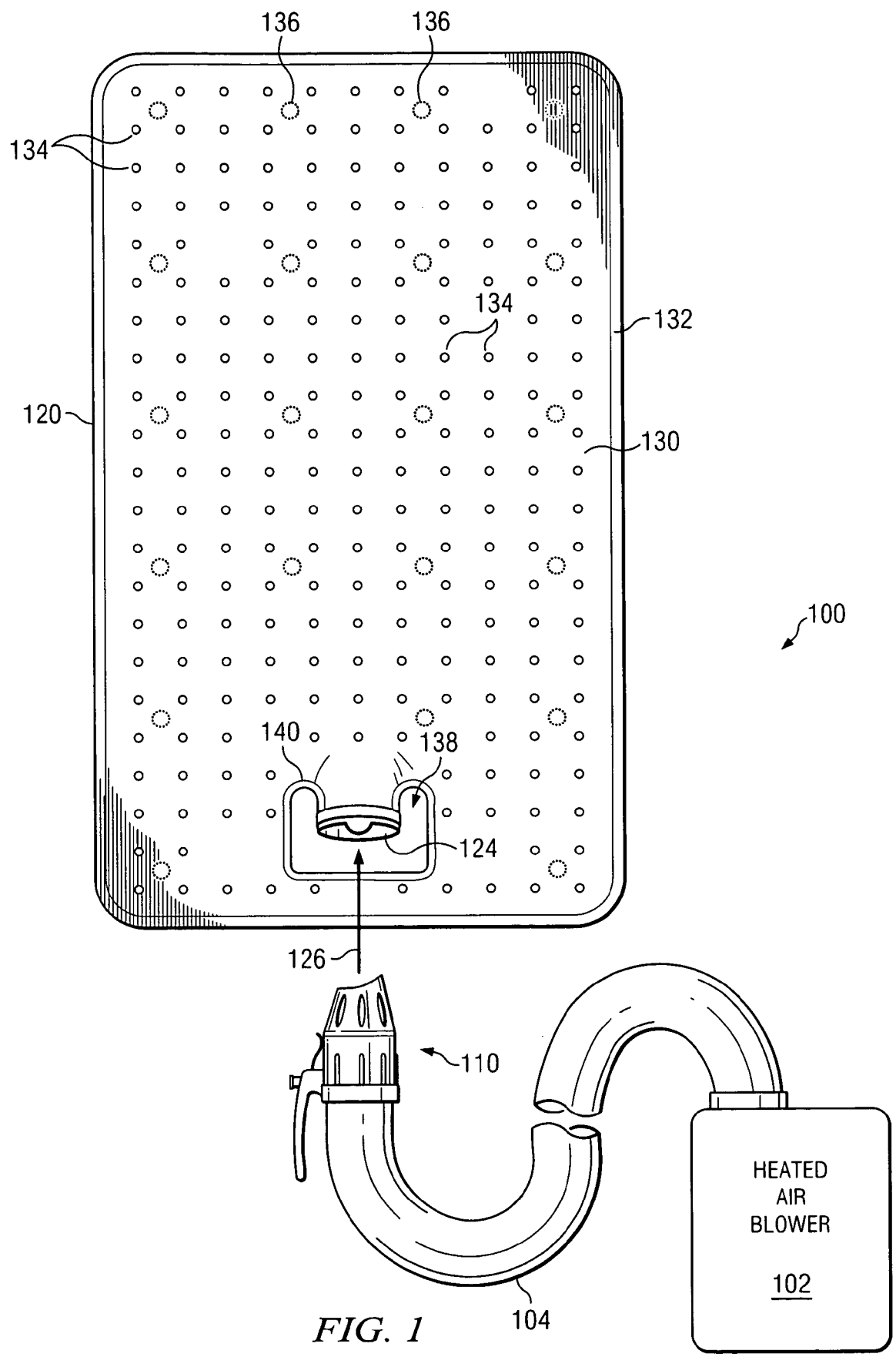
FIG. 1 depicts a warming blanket assembly in accordance with one aspect of the present technique.

Turning now to the drawings, FIG. 1 depicts one embodiment of a warming assembly 100 that includes a heated air blower 102, a hose 104, a nozzle 110, and a convective air warming blanket 120. An example, of a commercially distributed device suitable for use as heated air blower 102 is the WarmTouch® 5200/5300 series of warming units from the Nellcor division of Tyco Healthcare. For example, in an embodiment of warming assembly 100 that implements heated air blower 102 with a WarmTouch® 5300 warming unit, heated air may be provided to warming blanket 120 at predefined temperatures of 32° C., 38° C., 43°, or 45° C. As suggested by its name, heated air blower 102 produces and expels heated air. In the depicted embodiment, heated air from heated air blower 102 is provided to warming blanket 120 through the air hose 104 via an air inlet 124 or other opening in warming blanket 102. In particular, as depicted in the embodiment of FIG. 1, the nozzle 110 is configured to be inserted (as represented by arrow 126) into the air inlet 124. Once inserted into the air inlet 124, the nozzle 110 completes an air pathway from the heated air blower 102 through the hose 104 to the warming blanket 120.

In one embodiment, the warming blanket 120 includes a first sheet 130 bonded or otherwise attached to a second sheet along their common edges. In one implementation of the warming blanket 120, the first sheet 130 is a polyester material while the second sheet is a polypropylene. In an embodiment of the warming blanket 120 suitable for use in a surgical environment, the warming blanket 120 is approximately 150 to 220 centimeters long approximately 90 to 150 centimeters wide. Examples of implementations of convective air warming blankets suitable for use as the warming blanket 120 depicted in FIG. 1 are described in U.S. patent application Ser. No. 11/527,866 of Vardanega entitled, Use of Convective Air Warming System for Patient Care, filed on Sep. 27, 2006, and in U.S. patent application Ser. No. 11/528,217 of Vardanega entitled, Method and Apparatus for Inflating a Warming Blanket, filed on Sep. 27, 2006, both of which are incorporated by reference herein in their entirety.

In certain embodiments, the warming blanket 120 may be constructed using a die that cuts the first sheet 130 and the second sheet simultaneously so that the shape of the first sheet 130 coincides with the shape of the second sheet. In such an embodiment, an airtight seal 132 may be formed along the perimeter of the first and second sheets such that heated air entering the warming blanket 120 cannot exit along the perimeter of the warming blanket 120. Instead, the heated air blown into the warming blanket 120 exits via air openings 134 that are disposed (such as in an array) on at least one surface of the warming blanket 120.

In some embodiments, the perimeter seal 132 is formed by applying localized heat to the first and second sheets when the sheets are aligned and in contact with one another. In some of these embodiments, the localized heat causes the fusion of the materials forming the first and second sheets. In other embodiments, the localized heat causes the fusion of a coating or film (such as a polyethylene coating or film) applied to one or both of the first and second sheets. In such an embodiment, the coating or film, when heated, fuses with the material forming the other sheet or with a like coating or film disposed on the other sheet. Such an embodiment may be useful where the compositions of the first and second sheet are not easily fusible themselves but are each fusible with the film or coating composition, such as polyethylene.

Furthermore, some embodiments of the warming blanket 120 may include an array of weld points 136. The weld points 136 may be formed in the same manner as the perimeter seal 132, such as by the localized application of heat when the surfaces of the first and second sheets are in contact. As with the perimeter seal 132, the materials forming the first and second sheets may fuse directly or a film or coating on the sheets, such as the aforementioned polyethylene coating, may be fused to form the weld points 136. The weld points 136 serve to control the loft or range of separation of the first and second sheets when the warming blanket 120 is inflated.

As depicted in FIG. 1, the warming blanket 120 includes an air inlet region 138. The air inlet region 138 is generally sealed along the edges by an inlet seal 140 that circumscribes most but not the entire air inlet region 138. The portion of the air inlet region 138 that is not sealed is the air inlet 124. For example, referring to the embodiment depicted in FIG. 1, inlet seal 140 terminates at the edges of the air inlet 124, allowing the first and second sheets of the warming blanket 120 to be separated at the air inlet 124. Separation of the first and second sheets at the air inlet 124 results in the air inlet 124 being opened such that the nozzle 110 connected to the hose 104 may be inserted into the air inlet 124.

Figure 2:
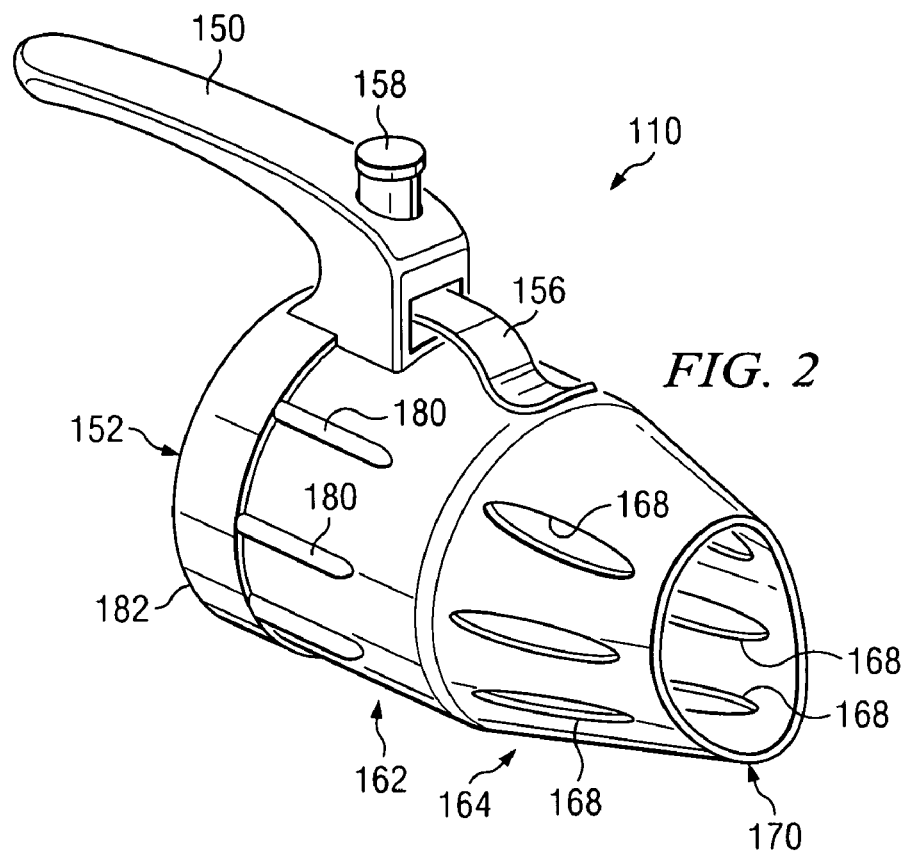
FIG. 2 is a perspective view of one embodiment of a nozzle, in accordance with one embodiment of the present technique.
Figure 3:
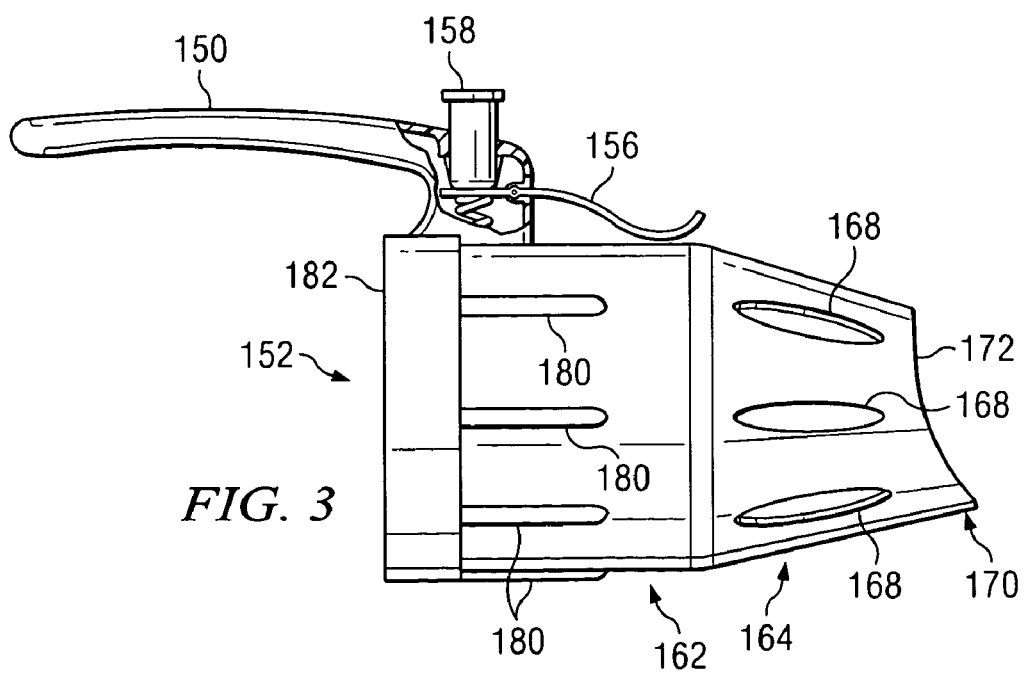
FIG. 3 is a side view of one embodiment of a nozzle, in accordance with one embodiment of the present technique.

Turning now to FIGS. 2 and 3, an embodiment of the nozzle 110 is depicted. While the nozzle 110 may be of different lengths and sizes in different embodiments, in one embodiment, the nozzle 110 is about 6 inches in length. In the depicted embodiment, the nozzle 110 includes a handle 150 connected to the nozzle body 152. In the depicted embodiment, the nozzle 110 includes a pivoting clip 156 attached to the handle 150. In one embodiment, a button 158 on the handle 150 causes part of the clip 156 to lift away from the nozzle body 152. However, when the button 158 is not depressed, a biasing mechanism (such as the spring 160 in the embodiment depicted in FIG. 3) biases the part of the clip 156 toward the nozzle body 152. As will be appreciated by those of ordinary skill in the art, other configurations of the biasing mechanism and other biasing mechanisms may be employed to actuate and bias the clip 156 in the manner described without departing from the scope of the present technique. In this manner the clip 156 can be moved between an open and closed position and thereby used to secure the nozzle 110 to the air inlet 124 of the warming blanket 120. In particular, in one embodiment, the clip 156 is configured to secure one of the sheets of the warming blanket 120 when the nozzle 110 is inserted into the air inlet 124.

In the depicted embodiment, one end of the handle 150 is affixed to the nozzle body 152. As will be appreciated by those of ordinary skill in the art, other handle configurations may be employed in accordance with the present technique. For example, handle configurations in which both ends of the handle 150 are affixed to the nozzle body 152 or configurations in which the unattached end of the handle 150 extends forward along the nozzle body 152 instead of extending rearward and away from the nozzle body 152 may also be employed. In one embodiment, the handle 150 and nozzle 110 are generally configured to enable or facilitate operation and maneuvering by a human operator using a single hand.

In the embodiment depicted in FIGS. 2 and 3, the nozzle body 152 includes a cylindrical section 162 and a tapered section 164. In one embodiment, the cylindrical section 162 is about 2.75 inches in diameter while the narrow end of the tapered section 164 is about 2.0 inches in diameter. As will be appreciated by those of ordinary skill in the art, other configurations of the nozzle body 152 are possible. For example, the nozzle body 152 may have a constant taper, and thus no cylindrical component. Likewise, the nozzle body 152 may not possess a circular cross-section throughout, but may instead have oval, elliptical or other cross-section shapes at different locations on the nozzle body 152. The taper of the nozzle body 152, either associated with a tapered section 164 or the nozzle body in general, facilitates insertion of the nozzle 110 into the air inlet.

In the depicted embodiment of FIGS. 2 and 3, a set of radially oriented vents 168 are provided on the nozzle 110, such as on the conical section 162. In one embodiment, seven vents 168 are provided on a tapered section 164. In one such embodiment, the vents 168 are 1.92 inches long and 0.375 inches wide. The vents 168 allow air flow through nozzle 110 to be substantially equivalent to the air flow through a similar nozzle having no taper. For example, in one experiment, the exit air speed was measured for heated air blown by a Warm-touch® 5300 heated air blower using both a conventional nozzle and a nozzle as depicted in FIGS. 2 and 3 having a tapered section 164 with seven radially disposed vents 168. Seven exit air speed measurements were made with each nozzle and the average exit air speed difference for the two nozzles was found to be only 0.14 m/s. In particular, the average exit air speed associated with the conventional nozzle was found to be 11.32 m/s while the average exit air speed associated with the tapered nozzle 110 with vents 168 was found to be 11.18 m/s.

Figure 4:
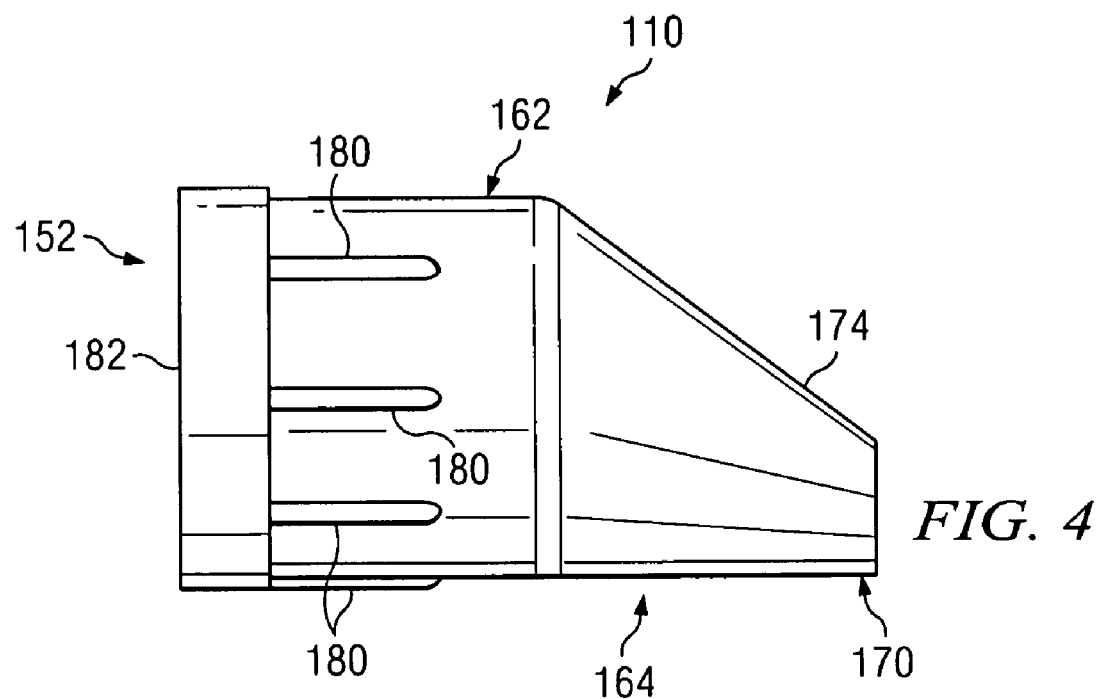
FIG. 4 is a side view of another embodiment of a nozzle, in accordance with one embodiment of the present technique.
Figure 5:
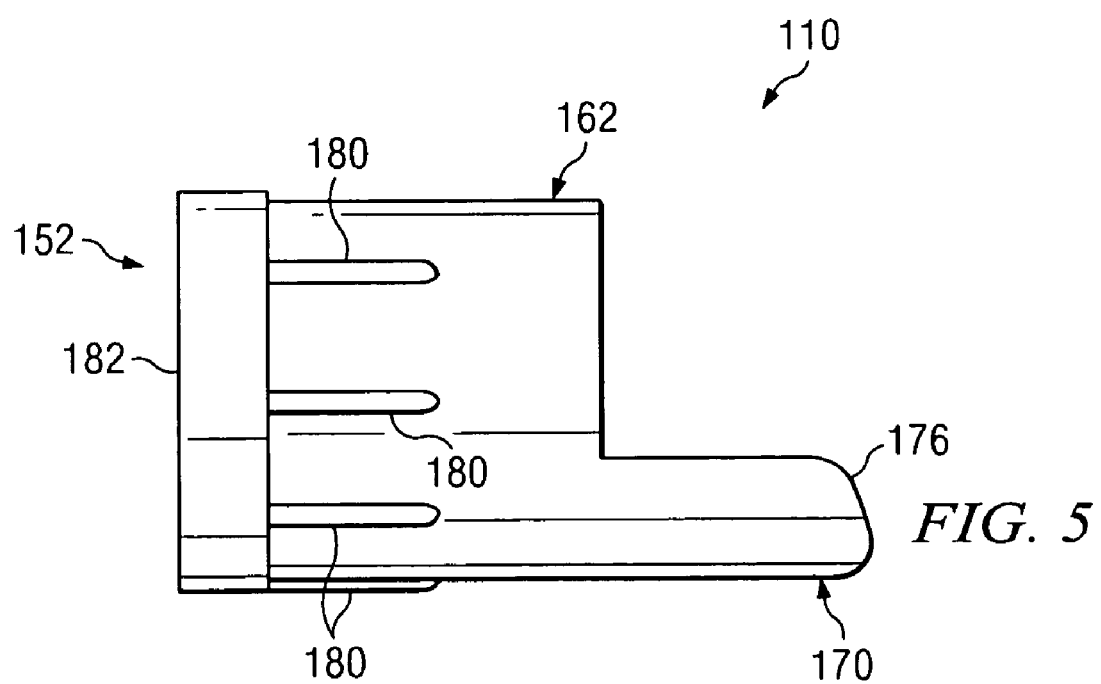
FIG. 5 is a side view of a further embodiment of a nozzle, in accordance with one embodiment of the present technique.

In one embodiment, the nozzle 110 is further configured to include a sheet separating projection 170, such as the concave surface 172 depicted in FIGS. 2 and 3. As shown in the side view of FIG. 3, the concave surface 172 is configured to function as a scoop that can separate the first and second sheets of warming blanket 120 when inserting the nozzle 110 into the air inlet 124. Although the embodiment of FIGS. 2 and 3 depicts a concave surface, other configurations of sheet separating projections 170 may be employed in other embodiments. For example, FIG. 4 depicts an alternative embodiment in which the sheet separating projection 170 is a straight edged tapered region 174, as compared to the concave surface of FIG. 3. Still other embodiments may include a sheet separating projection 170 that runs perpendicular to the central axis to the main nozzle body for a span before turning in either a straight line or curved fashion to form the leading edge 176 of the sheet separating projection 170 (see FIG. 5). As will be appreciated by those of ordinary skill in the art, such separating projections 170 facilitate the insertion of the nozzle 110 into the air inlet 124 by an operator by allowing the operator to separate the sheets forming the air inlet 124 using the nozzle itself.

Returning now to FIGS. 2 and 3, in the depicted embodiment, the nozzle 110 also includes a set of radially oriented ribs 180 located on the exterior surface of the cylindrical section 162. The ribs 180 facilitate handling and gripping of the nozzle 110 by a user. In one embodiment, seven ribs 180 are included on the nozzle 110. In such an embodiment, the ribs 180 may be approximately 1.4 inches long and may be provided as 0.22 inch diameter raised semi-circular protrusions. In one embodiment, the ribs 180 may begin at an edge of a collar section 182 on the nozzle 110.

Although the embodiment of nozzle 110 depicted in FIGS. 2 and 3 includes a cylindrical section 162 and a tapered section 164, other embodiments may employ alternative configurations to achieve a reduction in nozzle size between that portion of the nozzle attached to the hose 104 and that portion that is initially inserted into the air inlet 124. For example, no cylindrical section 162 may be provided on the nozzle body 152 and the nozzle body 152 may have a constant or varying degree of taper along most or all of its length.

The nozzle body 110 may be constructed of a durable, light weight, and hygienic material such as polycarbonate or other suitable polymer material. In one exemplary embodiment, the end of the nozzle body 152 proximate to the hose 104 has a diameter of approximately 3.15 inches while the end of the nozzle body 152 that is first inserted into the air inlet 124 has a diameter of approximately 2 inches. Likewise, in one embodiment, the overall length of the nozzle body 152 is approximately 6 inches or less.

As will be appreciated by those of ordinary skill in the art, medial personnel may operate an embodiment of the nozzle 110, as described herein, by grasping the handle 150, such as with a single hand, and maneuvering the nozzle 110 such that the sheet separating projection 170 separate the sheets forming the air inlet 124 of a warming blanket 120. The medical personnel may than actuate the button 158 to pivot the clip 156 to its open position and advance the nozzle 110 into the air inlet 124. The medical personnel may then release the button 158 to pivot the clip 156 to a closed position, thereby securing the nozzle 110 to the warm blanket 120.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A warming assembly, comprising:
a heated air blower configured to blow heated air;
a warming blanket comprising an air inlet; and
a hose configured to connect the heated air blower and the warming blanket, wherein the hose comprises a nozzle on an end of the hose that is inserted into the air inlet, wherein the nozzle comprises a projection configured to separate two sheets that form the air inlet.

2. The warming assembly of claim 1, wherein the projection comprises a concave region.

3. The warming assembly of claim 1, wherein the projection is asymmetric with respect to a plane intersecting a central axis of the nozzle.

4. The warming assembly of claim 1, wherein the projection comprises a tapered region.

5. The warming assembly of claim 1, wherein the nozzle comprises a tapered region configured to allow air to flow at substantially the same air flow rate as would be achieved with a nozzle having no tapered region.

6. The warming assembly of claim 5, wherein the nozzle comprises a plurality of vents configured to provide an air flow rate of about 11.18 m/s.

7. A nozzle configured for use with an air hose, the nozzle comprising a projection configured to separate two sheets that form an air inlet of a warming blanket.

8. The nozzle of claim 7, wherein the projection comprises a concave region.

9. The warming assembly of claim 7, wherein the projection is asymmetric with respect to a plane intersecting a central axis of the nozzle.

10. The nozzle of claim 7, wherein the projection comprises a tapered region.

11. The nozzle of claim 7, wherein the nozzle comprises a tapered region configured to allow air to flow at substantially the same air flow rate as would be achieved with a nozzle having no tapered region.

12. The nozzle of claim 11, wherein the nozzle comprises a plurality of vents configured to provide an air flow rate of about 11.18 m/s.

13. A method for inserting a nozzle into an air inlet, comprising:
    separating two sheets forming an air inlet of a warming blanket with a projecting portion of a nozzle of an air hose;
    inserting the nozzle between the separated sheets of the air inlet; and
    fastening a clip of the nozzle onto one of the sheets forming the air inlet when the nozzle is inserted between the separated sheets of the air inlet.

14. The method of claim 13, wherein the nozzle comprises a tapered region comprising a plurality of vents.

15. The method of claim 14, comprising:
    blowing air from a heated air blower through the air hose and nozzle into the warming blanket at substantially the same air flow rate as would be achieved with a nozzle having no tapered region.

* * * * *